United States Patent

Podszun et al.

Patent Number: 5,548,001
Date of Patent: Aug. 20, 1996

[54] SWELLABLE BEAD POLYMER CONTAINING FILLERS

[75] Inventors: Wolfgang Podszun; Jens Winkel, Cologne; Michael Müller, Bayerwerk, all of Germany

[73] Assignee: Heraeus Kulzer GmbH & Co. KG, Hanau, Germany

[21] Appl. No.: 652,336

[22] Filed: Feb. 7, 1991

[30] Foreign Application Priority Data

Feb. 15, 1990 [DE] Germany ............... 40 04 678.8

[51] Int. Cl.⁶ ............... C08K 3/20; C08L 33/08; B32B 5/16
[52] U.S. Cl. ............... 523/116; 523/115; 523/205; 523/220; 523/221; 526/323.1; 526/323.2; 433/228.1
[58] Field of Search ............... 526/323.1, 323.2; 523/220, 221, 116, 205, 115; 433/228.1

[56] References Cited

U.S. PATENT DOCUMENTS 5,039,475  8/1991  Chida et al. ............... 523/205
5,039,718  8/1991  Ashley et al. ............... 523/205

*Primary Examiner*—Paul R. Michl
*Assistant Examiner*—Andrew E. C. Merriam
*Attorney, Agent, or Firm*—Sprung Horn Kramer & Woods

[57] ABSTRACT

In the filling of a buccal area tooth, wherein a polymerizable dental material containing a cross-linked bead poller is filled into the tooth and permitted to set, wherein the bead polymer has an average particle diameter of 2 to 100 μm an inorganic filler content of to 50% by weight and a degree of swelling of 50 to 2000%, measured in THF, and is synthesized from A: 10 to 78% by weight of $C_1$–$C_2$-alkyl (meth)acrylate B: 5 to 10% by weight of $C_3$–$C_{12}$-alkyl (methacrylate)

C: 1 to 30% by weight of cross-linker

D: 10 to 75% by weight of an inorganic filler, and

E: 0 to 30% by weight of at least one other ethylenically unsaturated monomer.

The cross-linked bead polymer is new, has a solid consistency, is storable and is especially useful for filling teeth in the buccal area.

3 Claims, No Drawings

SWELLABLE BEAD POLYMER CONTAINING FILLERS

The invention relates to swellable bead polymers containing fillers, to their preparation and to their use in polymerizable dental materials. It is known, for example, from U.S. Pat. No. 4,396,377, to employ cross-linked swellable bead polymers based on methacrylic acid esters in dental materials, in particular for the preparation of artificial teeth and prostheses. As these bead polymers are not reinforced by inorganic fillers, the materials prepared therefrom show mechanical strengths which are too limited for some areas of use such as, for example, use as a filling material in the buccal tooth area.

Cross-linked bead polymers containing fillers are described in DE-OS (German Published Specification) 2,849,936 and DE-OS (German Published Specification) 3,201,109. These bead polymers are outstandingly suitable as components of dental filling materials. By mixing with monomeric binders, pasty preparations are obtained which have good processing properties and can be converted by setting into materials with high transparency and high mechanical strength (DE-OS (German Published Specification) 2,850,917). The known-bead polymers containing fillers are not swollen or are swollen only to a very small extent by the monomers of the polymerizable dental materials.

For use as a dental filling material in the buccal tooth area, polymerizable pasty preparations having a solid consistency are particularly advantageous as these can be processed according to the packing technique and can be easily modelled.

Polymerizable preparations having a solid consistency can only be prepared with difficulty industrially as, owing to the high heat of mixing, the low heat conductivity and the low oxygen diffusion rate, undesired premature polymerization of the preparation can occur during the preparation process.

Premature polymerization can actually be influenced within certain limits by the industrial boundary conditions, such as batch size, geometry of the mixing apparatus, mixing efficiency and temperature control, but a fundamental solution of the problem is not possible in this way.

An object on which the present invention is based is therefore to make available a component for dental materials, in particular for dental filling materials, which makes possible or facilitates the production of preparations having a particularly solid consistency. A further object is to make available a component for dental materials which influences both the processing properties and the final intrinsic properties of the material in an advantageous manner.

These objects are achieved by the use of crosslinked bead polymers, which are characterized in that they have an average particle diameter of 2 to 100 μm, a content of inorganic filler of 10 to 75% by weight and a degree of swelling of 50 to 2000%, measured in THF.

The cross-linked bead polymers are preferably synthesized from the following components:
A: 10 to 78% by weight of $C_1$–$C_2$-alkyl (meth)acrylate
B: 5 to 50% by weight of $C_3$–$C_{12}$-alkyl (meth)acrylate
C: 1 to 30% by weight of cross-linker
D: 10 to 75% by weight of inorganic fillers
E: 0 to 30% by weight of other ethylenically unsaturated monomers.

Both the acrylate and the methacrylate are meant by the designation (meth)acrylate, and $C_1$–$C_2$-alkyl (meth)acrylates (component A) are methyl acrylate, methyl methacrylate, ethyl acrylate and ethyl methacrylate. Methyl methacrylate is preferred.

$C_3$–$C_{12}$-Alkyl (meth)acrylates (component B) are aliphatic, branched aliphatic and cycloaliphatic esters of acrylic and methacrylic acid. Examples which may be mentioned are: n-propyl acrylate, i-propyl acrylate, i-propyl methacrylate, n-butyl acrylate, n-hexyl acrylate, n-hexyl methacrylate, 2-ethylhexyl acrylate, n-decyl methacrylate, n-decyl acrylate, n-dodecyl methacrylate and cyclohexyl methacrylate.

Alkyl (meth)acrylates in which the carbon chain is interrupted by oxygen, such as 2-methoxyethyl methacrylate, 3-methoxybutyl methacrylate and ethyl triglycol methacrylate, are also suitable.

Cross-linkers (component C) are (meth)acrylates having 2 or more, preferably 2 to 4, polymerizable double bonds in the molecule, such as, for example: ethylene glycol dimethacrylate, diethylene glycol dimethacrylate, triethylene glycol dimethacrylate, glycerol dimethacrylate, glycerol trimethacrylate, trimethylolpropane trimethacrylate, trimethylolpropane triacrylate, pentaerythritol dimethacrylate, pentaerythritol trimethacrylate, pentaerythritol tetramethacrylate, derivatives of bisphenol A, such as bisphenol A dimethacrylate and bisphenol A diglycol dimethacrylate, bisphenol A diglycidyl dimethacrylate, urethane methacrylates which can be prepared by reaction of diisocyanates and hydroxyalkyl methacrylates, such as

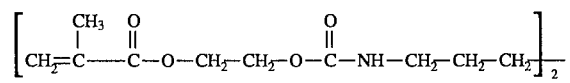

and reaction products of polyols, diisocyanates and hydroxyalkyl methacrylates (DE-A 3,703,080, DE-A 3,703,130 and DE-A 3,703,120).

Suitable inorganic fillers (component D) are colorless inorganic substances, such as quartz, cristobalite, quartz glass, highly disperse silicic acid, silicates, aluminosilicates, silicate glasses and glass ceramics. The fillers in general have an average particle diameter of 0.01 to 10 μm, preferably 0.02 to 5 μm. Preferred fillers are those based on $SiO_2$ which have a high specific surface area, for example 50 to 400 $m^2/g$, measured by the BET method.

In order to achieve a high degree of filling and a favorable property spectrum, fillers having a bimodal distribution or filler combination can be employed.

The inorganic fillers are preferably used in adhesion promoter-treated form. Suitable adhesion promoters are, for example, silane and titanate compounds, such as trimethylchlorosilane, hexamethyldisiloxane, 3-aminopropyltrimethoxysilane, butyl titanate and isopropyl titanate. Adhesion promoters having polymerizable groups, such as vinyltrimethylsiloxane, allyltrimethoxysilane and γ-methacryloyloxypropyltrimethoxysilane are particularly highly suitable.

The quantity of adhesion promoters is 0.1 to 10% by weight, preferably 0.5 to 5% by weight, relative to the inorganic filler.

The cross-linked bead polymers can contain up to 30%, preferably up to 20%, of other ethylenically unsaturated monomers which are copolymerizable with the components A–C as component E. Examples which may be mentioned are: styrene, α-methylstyrene, vinyltoluene, acrylonitrile, methacrylonitrile, vinyl acetate and vinyl propionate.

The present invention also relates to the process for the preparation of the bead polymers according to the invention. This process is characterized in that a mixture I of
A: 10 to 78 parts by weight of $C_1$–$C_2$-alkyl (meth)acrylate
B: 5 to 50 parts by weight of $C_3$–$C_2$-alkyl (meth)acrylate
C: 1 to 30 parts by weight of cross-linker D: 10 to 75 parts by weight of inorganic filler E: 0 to 30 parts by weight of other ethylenically unsaturated monomers and F: 50 to 1000 parts by weight of non-aqueous diluent is dispersed in an aqueous polymer solution II and polymerized by the suspension polymerization procedure using an initiator.

Suitable non-aqueous diluents (component F) are liquids which at least partially dissolve the monomers readily and non-cross-linked polymers which are synthesized from the components A, B and E. The solution properties can be defined by the so-called solubility parameter (H. G. Elias, Makromoleküle (Macromolecules), pp. 192–196 (1981)). Diluents having a parameter of from 8 to 15 ($cal^{0.5}cm^{-1.5}$), preferably of from 8.5 to 13 ($cal^{0.5}cm^{-1.5}$) are used for the process according to the invention.

The following diluents may be mentioned as examples. Amyl acetate, butyl acetate, propyl acetate, ethyl acetate, ethyl propionate, butan-2-one, pentanol, hexanol, heptanol, octanol, 1,2-dichloroethane, tetrachloroethane, dichloromethane, trichloromethane, toluene and chlorobenzene. Toluene is particular highly suitable.

The amount of the diluents employed in addition to the amount of cross-linker influences the degree of swelling very substantially. In general, the diluent is employed in amounts of from 50 to 1000% by weight, preferably 100 to 500% by weight, relative to the total of the components A–E.

In the first step of the process according to the invention, the components A-F are intensively mixed. In order to achieve a good dispersion of the filler, mixing apparatuses are preferably used which produce high shearing forces, for example high-speed stirrers, rotor/stator mixers or ball mills.

In a particular embodiment of the process, the surface treatment of the filler is carried out using the abovementioned adhesion promoters in the dispersion obtained. In this case, of course, the catalysts necessary for the surface treatment are employed. Amines, for example, such as dicyclohexylamine are highly suitable catalysts for the surface treatment using alkylsilane compounds.

Suitable initiators for starting the polymerization are free radical generators known per se, such as aliphatic azodicarboxylic acid derivatives such as azobisisobutyronitrile or azodicarboxylic acid esters, peroxides such as lauroyl peroxide, succinyl peroxide, dibenzoyl peroxide, p-chlorobenzoyl peroxide, 2,4-dichlorobenzoyl peroxide, methyl ethyl ketone peroxide, methyl isobutyl ketone peroxide, cyclohexanone peroxide, acetylacetone peroxide, alkyl esters of peracids such as tert.-butyl perpivalate, tert.-butyl peroctoate, tert.-butyl perbenzoate, tert.-butyl perisononanoate, mono-tert.-butyl permaleate, tert.-butyl peracetate, percarbonates such as dicyclohexyl and diisopropyl percarbonate, hydroperoxide such as tert.-butyl or cumene hydroperoxide, isophthalic monoperacid or acetylcyclohexane-sulphonyl peroxide.

Mixtures of polymerization initiators having different decomposition temperatures are also highly suitable. The initiator is added to the mixture of the components A–F in amounts of 0.01 to 3% by weight, preferably 0.1 to 1.5% by weight, relative to the total of the components A, B, C and E.

The activated mixture is dispersed in an aqueous polymer solution. The ratio of organic phase to aqueous phase should in this case as a rule be 1:1 to 1:10, preferably 1:1.5 to 1:4.

The dispersion aids employed in suspension polymerization are used in the aqueous dispersion. A list of suitable substances is found in the literature, for example in Houben-Weyl, Methoden der organischen Chemie (Methods of organic chemistry), Volume XX, 1987. For example, polyvinylpyrrolidone, Na polymethacrylate, partially hydrolyzed polyvinyl acetates having degrees of hydrolysis of 75 to 98%, copolymers of methacrylic acid and methacrylic acid esters of lower alcohols and cellulose derivatives such as carboxymethyl cellulose are highly suitable. Copolymers of methacrylic acid and $C_1$–$C_4$-alkyl methacrylates in the form of their Na salts are particularly preferred.

The polymerization is started by heating to the decomposition temperature of the polymerization initiators. Cooling must be carried out, if necessary, during the commencing exothermic reaction. It may be advantageous to carry out the polymerization at elevated pressure, for example at a nitrogen pressure of 2 to 6 bar.

The bead polymer can be obtained from the polymerized dispersion in a manner known per se by decanting, filtering, washing and drying. The diluent is then completely removed by sucking it off in vacuo.

It is particularly advantageous to remove the diluent from the polymerized dispersion by distillation before the isolation of the bead polymer.

This can be accomplished particularly easily with diluents which have a lower boiling point than water or form an azeotrope with water.

The bead polymers according to the invention have a degree of swelling of 50 to 2000% by weight, preferably 100 to 1000% by weight. The degree of swelling is understood as meaning the absorption capacity for liquid.

$$\text{Degree of swelling} = \frac{\text{weight of absorbed liquid}}{\text{weight of the polymer}} \times 100$$

The degree of swelling is measured by the absorption capacity for tetrahydrofuran at 20° C.

The bead polymers according to the invention are suitable for the production of polymerizable dental materials, in particular plastic dental filling materials having a solid consistency.

The invention further relates to polymerizable dental materials, in particular plastic dental filling materials, containing 20 to 60% by weight, preferably 25 to 50% by weight, of monomeric binder, 30 to 78% by weight, preferably 50 to 70% by weight, of filler, 0.5 to 30% by weight, preferably 1 to 10% by weight, of cross-linked bead polymer and, if desired, additives known per se, characterized in that the cross-linked bead polymer fulfills the abovementioned criteria.

The polymerizable dental materials according to the invention can be adjusted to any desired solid consistency. They can be modelled easily and can be processed according to the packing technique, as a result of which important criteria for use as a dental filling material in the buccal tooth area are fulfilled.

The dental materials according to the invention are prepared by mixing the starting components in customary mixing apparatuses, such as, for example kneaders, the following procedure proving particularly advantageous:

The starting components are mixed in a kneader to give a material which is readily capable of flow and has a consistency which is easily controllable industrially. This material is optionally colored, divided into portions and packed. The dental material obtains the final solid consistency as a result of subsequent maturation. The extent of the subsequent strengthening during the maturation can be controlled by the degree of swelling and the amount of the bead polymer according to the invention employed.

The subsequent strengthening is concluded after a certain period of time, the so-called maturation time. After this time, the consistency is constant over long periods of time, for example 12 months. The maturation time as a rule lasts for some days at room temperature. By increasing the temperature to, for example, 50° C. or 60° C., it can be reduced to hours. In addition, maturation at elevated temperature leads to a stable consistency level.

Suitable fillers for the dental materials according to the invention are the pure inorganic fillers discussed hereinabove as component D. Their average particle diameter should lie in the range from 0.01 to 30 µm, preferably 0.01 to 10 µm, particularly preferably 0.02 to 5 µm. Fillers treated with adhesion promoters are preferably employed. Additionally, highly suitable fillers are bead polymers containing filler according to DE-OSen (German Published Specifications) 2,849,936 and 3,201,109, and furthermore microporous fillers according to DE-OS (German Published Specification) 3,430,801.

Suitable monomeric binders are primarily esters of acrylic acid or methacrylic acid. (Meth)acrylic acid esters having 2 or more (meth)acrylic groups in the molecule are preferred, and examples which may be mentioned are: triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis(p-(2'-hydroxy-3'-methacryloyloxypropoxy)phenyl)propane, 2,2-bis(p-(2'-methacryloyloxyethoxy)phenyl)-propane, trimethylolpropane tri(meth)acrylate, bis-((meth)acryloyloxymethyl)tricyclo-[5.2.1.0$^{2.6}$]decane (according to DE-OS (German Published Specification) 2,931,925 and DE-OS (German Published Specification) 2,931,926) and 1,3-di((meth)acryloyloxypropyl)- 1,1,3,3-tetra-methyldisiloxane.

Highly suitable monomeric binders are also urethane (meth)acrylates according to DE-OS (German Published Specifications) 3,625,202, 3,703,120, 3,636,189, 3,703,680 and 3,703,130.

It is preferred to employ mixtures of various (meth)acrylic acid esters.

The dental materials according to the invention contain free radical generators known per se as setting initiators. Setting initiators for polymerization by light, for example UV, visible light or laser light, are preferred.

Appropriate photopolymerization initiators are known; preferably in this case these are carbonyl compounds, such as benzoin and its derivatives, in particular benzoin methyl ether, benzil and benzil derivatives, for example 4,4-oxydibenzil or other dicarbonyl compounds, for example diacetyl, 2,3-pentanedione or metal carbonyls, quinones or their derivatives. The proportion of such photopolymerization initiators is preferably about 0.01 to about 5% by weight of the total composition.

These preparations which can be set by light, i.e. polymerizable preparations, preferably also still contain substances which accelerate the polymerization reaction in the presence of photopolymerization initiators. Known accelerators are, for example, aromatic amines such as p-toluidine and dimethyl-p-toluidine, trialkylamines such as trihexylamine, polyamines, such as N,N,N'N'-tetraalkyl -alkylenediamine, barbituric acid and dialkylbarbituric acids and sulphimides, preferably in an amount of about 0.01 to about 5% by weight of the total composition.

It is finally expedient to add UV stabilizers to the materials according to the invention in order to avoid subsequent darkening during ageing.

A particularly suitable UV stabilizer is 2-hydroxy-4-methoxybenzophenone. Another preferred material is 2-(2'-hydroxy-5'-methylphenyl)-benzotriazole; but in principle any physiologically inert UV-absorbing agent is suitable for this purpose. Thus, examples which may also be mentioned are hydroquinone, p-benzoquinone, p-butylhydroxytoluene, and the like. The latter compound, for example, can also act as an antioxidant in the filling.

A review of the substances customarily employed in dental filling materials is found in the article by R. L. Bowen in the Journal of Dental Research, Vol. 58/5 (May 1979), pp. 1493–1503, and the attached supplement by J. F. Lann, pp. 1504–1506, and the literature references cited therein.

In order to achieve specimens of the dental materials which are as true to life as possible, they also contain, if necessary, a small proportion of colorants or pigments.

When using large proportions of multi-functional monomers (cross-linkers) and for certain purposes of use, it may be advantageous to add plasticizers to the polymerizable materials according to the invention to reduce the brittleness. High molecular weight plasticizers known per se are primarily highly suitable, particularly those based on polyurethanes, polycarbonates, polyesters and polyethers. Polyesters and polyester carbonates which are described in DE-OS (German Published Specification) 3,316,851 are preferred.

EXAMPLE 1

Preparation of a bead polymer according to the invention a) Monomer mixture 34.5 g of methyl methacrylate, 37.5 g of isobutyl methacrylate, 18 g of 2,2-bis[p-(2'-hydroxy-3'-methacryloxypropoxy)phenyl]propane (bisGMA), 12.6 g of γ-methacryloxypropyltrimethoxysilane, 2 g of dicyclohexylamine and 100 g of n-pentanol are weighed into a reaction vessel which is equipped with a high-speed stirrer and mixed. 210 g of barium glass filler having an average particle diameter of 1.3 µm are dispersed into the solution obtained. The dispersion is stirred at 50° C. for 5 hours, then cooled to 20° C. and activated with 1.88 g of dibenzoyl peroxide and 1.88 g of dicyclohexyl percarbonate.

b) Bead polymerization 32 g of poly(methyl methacrylate-co-methacrylic acid) in 1300 ml of water are dispersed in a reaction vessel using an anchor impeller stirrer. A quantity of 1N NaOH is added such that a clear solution having a pH of 8 is formed. The monomer mixture is emulsified in this solution. The temperature is increased to 75° C. in the course of 15 minutes. During the commencing exothermic reaction, the mixture is cooled vigorously so that the temperature is kept in the range from 75° C. to 85° C. After the reaction subsides, the mixture is subsequently stirred at 85° C. for 2 hours.

The bead polymer formed is isolated by sedimenting and decanting off, washed thoroughly with water and dried in vacuo (0.1 torr) at 80° C. to constant weight, the pentanol being completely removed. 260 g of bead polymer having an average particle size of 22 µm, a filler content of 70% and a degree of swelling, determined in THF, of 130% are obtained.

EXAMPLE 2

Example 1 is repeated, toluene being employed instead of pentanol. Before the isolation of the bead polymer, the main amount of toluene is removed by distillation. 255 g of bead polymer having an average particle size of 28 µm, a filler content of 70% and a degree of swelling of 160% are obtained.

EXAMPLE 3

Activated monomer mixtures of the following compositions are prepared by the procedure given in Example 1.

|  | A | B | C |
|---|---|---|---|
| Methyl methacrylate | 80 g | 80 g | 80 g |
| Isopropyl methacrylate | 76 g | 76 g | 76 g |
| Bis-GMA | 39 g | 39 g | 39 g |
| γ-methacryloxypropyl-trimethoxysilane | 6.3 g | 6.3 g | 6.3 g |
| Dicyclohexylamine | 1 g | 1 g | 1 g |
| Highly disperse silica (BET surface area 50 m$^2$/g) | 105 g | 105 g | 105 g |
| Toluene | 195 g | 244 g | 293 g |

The activated monomer solutions are reacted to give bead polymers as described in Example 1b, the main amount of the toluene being removed by distillation before the isolation of the bead polymer.

Bead polymers having the following characteristics are obtained:

|  | A | B | C |
|---|---|---|---|
| Yield | 261 g | 274 g | 281 g |
| Average particle size | 14 μm | 18 μm | 24 μm |
| Degree of swelling in THF | 205% | 260% | 280% |
| Filler content | 34.5% | 34.5% | 34.8% |

EXAMPLE 4

3.0 g of a mixture of 70 parts by weight of the reaction product of 2(3),7(8)bis(isocyanatomethyl)tricyclo(5.2.1.0$^{2.6}$)decane with 2-hydroxyethyl acrylate, 20 parts by weight of trimethylolpropane triacrylate and 10 parts by weight of neopentylglycol dimethacrylate are processed to give a paste using 0.45 g of silanized highly disperse silicic acid (Aerosil 300 Degussa) and 6 g of silanized barium glass (GM 27884 Schott).

0.1 g or 0.5 g of bead polymer from Example 3 is incorporated into 10 g of this paste.

These pastes are then stored in a drying cabinet at 45° C. and the swelling is monitored using a penetrometer (SUR, measurement after 30 sec., 30 scale divisions (sc.div.)=3 mm penetration).

The swollen pastes—especially that containing 5% bead polymer—show the packable, adhesion—free processing behavior desired for a buccal tooth composite.

| Storage time | 1% bead polymer Example 3 A | 1% bead polymer Example 3 B | 1% bead polymer Example 3 C | 5% bead polymer Example 3 A | 5% bead polymer Example 3 B | 5% bead polymer Example 3C |
|---|---|---|---|---|---|---|
| Starting value | 29.3 sc. div. | 29.3 sc. div. | 29.5 sc. div. | 29.4 sc. div. | 29.3 sc. div. | 29.5 sc. div. |
| 18 hours 45° C. | 29.0 sc. div. | 28.6 sc. div. | 28.6 sc. div. | 29.1 sc. div. | 27.1 sc. div. | 18.1 sc. div. |
| 6 days 45° C. | 27.1 sc. div. | 27.1 sc. div. | 27.1 sc. div. | 25.8 sc. div. | 15.4 sc. div. | 10.7 sc. div. |
| 11 days 45° C. | 27.7 sc. div. | 26.9 sc. div. | 26.4 sc. div. | 25.2 sc. div. | 16.1 sc. div. | 11.6 sc. div. |

It will be understood that the specification and examples are illustrative but not limitative of the present invention and that other embodiments within the spirit and scope of the invention will suggest themselves to those skilled in the art.

What is claimed is:

1. A cross-linked bead polymer having an average particle diameter of 2 to 100 μm containing an inorganic filler content of 10 to 75% by weight and a degree of swelling of 50 to 2000%, measured in THF, synthesized from A: 10 to 78% by weight of $C_1$–$C_2$-alkyl (meth)acrylate, B: 5 to 50% by weight of $C_3$–$C_{12}$-alkyl (meth)acrylate, C: 1 to 30% by weight of cross-linker;

10 to 75% by weight of an inorganic filler; and

E: 0 to 30% by weight of at least one other ethylenically unsaturated monomer.

2. In the filling of a tooth, wherein a polymerizable dental material containing a cross-linked bead polymer is filled into the tooth and permitted to set, the improvement wherein the bead polymer is a bead polymer according to claim 1.

3. A polymerizable dental material by weight comprising 20 to 60% of a monomeric binder, 30 to 78% of a filler and 0.5 to 30% of a cross-linked bead polymer according to claim 1.

* * * * *

UNITED STATES PATENT AND TRADEMARK OFFICE
CERTIFICATE OF CORRECTION

PATENT NO. : 5,548,001
DATED      : August 20, 1996
INVENTOR(S) : Podszun, et al.

It is certified that error appears in the above-indentified patent and that said Letters Patent is hereby corrected as shown below:

Title Page         U.S. PATENT DOCUMENTS:  Insert
        -- 4,308,190 12/1981 Walkowiok et al...523/116
           4,394,465 7/1983 Podszun et al...523/220
           4,396,476 8/1983 Roemer et al....523/116
           4,937,144 6/1990 Podszun et al...523/116--
           and delete " 5,039,475 " and substitute
           -- 5,037,475

Title Page    ABSTRACT:  Line 5 after " of " (first
              occurrence) insert -- 10 --

Col. 8, line 41   Before " 10 " insert -- D: --

Signed and Sealed this

Eleventh Day of March, 1997

Attest:

BRUCE LEHMAN

*Attesting Officer*          *Commissioner of Patents and Trademarks*